US009080166B2

(12) United States Patent
Kim et al.

(10) Patent No.: US 9,080,166 B2
(45) Date of Patent: *Jul. 14, 2015

(54) COMPOSITE OF ENZYME AND FIBER MATRIX WITH THREE-DIMENSIONAL STRUCTURE, METHOD FOR PRODUCING THE SAME AND USE THEREOF

(75) Inventors: Jungbae Kim, Seoul (KR); Hyeong-Seok Kim, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/698,734

(22) PCT Filed: Apr. 19, 2011

(86) PCT No.: PCT/KR2011/002785
§ 371 (c)(1),
(2), (4) Date: Feb. 4, 2013

(87) PCT Pub. No.: WO2011/145809
PCT Pub. Date: Nov. 24, 2011

(65) Prior Publication Data
US 2013/0130284 A1 May 23, 2013

(30) Foreign Application Priority Data

May 20, 2010 (KR) .......................... 10-2010-0047337
Apr. 19, 2011 (KR) .......................... 10-2011-0035980

(51) Int. Cl.
| | |
|---|---|
| *C12N 11/04* | (2006.01) |
| *C12N 11/08* | (2006.01) |
| *C12N 11/10* | (2006.01) |
| *C12N 11/12* | (2006.01) |
| *C12Q 1/00* | (2006.01) |
| *H01M 8/02* | (2006.01) |
| *H01M 8/16* | (2006.01) |
| *H01M 4/90* | (2006.01) |

(52) U.S. Cl.
CPC ............... *C12N 11/04* (2013.01); *C12N 11/08* (2013.01); *C12N 11/10* (2013.01); *C12N 11/12* (2013.01); *C12Q 1/001* (2013.01); *H01M 4/9008* (2013.01); *H01M 8/0239* (2013.01); *H01M 8/16* (2013.01); *Y02E 60/527* (2013.01)

(58) Field of Classification Search
None
See application file for complete search history.

(56) References Cited

U.S. PATENT DOCUMENTS

| | | | |
|---|---|---|---|
| 8,642,308 B1 * | 2/2014 | Atanassov et al. ............ | 435/181 |
| 2004/0241436 A1 * | 12/2004 | Hsieh et al. .................. | 428/361 |
| 2008/0318294 A1 * | 12/2008 | Kim .............................. | 435/188 |

FOREIGN PATENT DOCUMENTS

WO WO-9306925 4/1993

OTHER PUBLICATIONS

Kim et al., Highly stable enzyme precipitate coatings and their electrochemical applications, Biosensors and Bioelectronics, 26, 1980-1986, Oct. 15, 2010.*
Kim et al., Highly stable trypsin-aggregate coatings on polymer nanofibers for repeated protein digestion, Proteomics, 9(7), 1983-1900, 2009.*
Zhao et al., Polyaniline nanofibers: Synthesis, Characterization and Application to direct electron transfer of Glucose oxidase, J. Phys. Chem. C, 2009, 113, 4987-4966.*
Xu et al., Dendrimer-encapsulated Pt nanoparticles/polyaniline nanofibers for glucose detection, Journal of Applied Polymer Science, vol. 109, 1802-1807, 2008.*
Jung et al., Formation of Cross-Linked Chloroperoxidase Aggregates in the Pores of Mesocellular Foams: Characterization by SANS and Catalytic Properties, ChemSusChem, 2, 161-164, 2009.*
Cao, L., et al.; "Immobilised enzymes: carrier-bound or carrier-free?" Current Opinion in Biotechnology; vol. 14, No. 4; pp. 387-394; dated Aug. 2003.
Jung., D., et al.; "Formation of Cross-Linked Chloroperoxidase Aggregates in the Pores of Mesocellular Foams: Characterization by SANS and Catalytic Properties;" Chemsuschem; vol. 29, No. 2; pp. 161-164; dated Feb. 2009.
Kim, J., et al.; "Challenges in biocatalysis for enzyme-based biofuel cells;" Biotechnology Advanced; vol. 24, No. 3; pp. 296-308; dated Jun. 2006; retrieved on. Feb. 7, 2013 from <www.uta.edu/biology/grover/classnotes/5101/Paper2for11-15.pdf>.
Kim, M. I., et al.; "Crosslinked enzyme aggregates in hierarchically-ordered mesoporous silica: A simple and effective method for enzyme stabilization;" Biotechnol. Bioeng.; vol. 96, No. 2; pp. 210-218; dated Feb. 2007; retrieved on Feb. 7, 2013 from <http://bcbd.kaist.ac.kr/BBS/Include/BBS_Download.php?file=pdf_02/upload/uproQGHo&_file=27.pdf&no=57893>.
International Search Report for Application No. PCT/KR2011/002785; dated Jan. 11, 2012.

* cited by examiner

*Primary Examiner* — Taeyoon Kim
*Assistant Examiner* — Srikanth Patury
(74) *Attorney, Agent, or Firm* — Novick, Kim & Lee, PLLC; Jae Youn Kim (57) ABSTRACT

Disclosed is a composite of enzyme and fiber matrix with three-dimensional structure. The composite of enzyme and fiber matrix with three-dimensional structure includes a significantly large amount of an enzyme loaded in and immobilized in/onto a matrix when compared to conventional composites. In addition, the immobilized enzyme is prevented from leaching from the matrix when an external impact is applied to the composite of enzyme and fiber matrix with three-dimensional structure. Therefore, the stability of the composite of enzyme and fiber matrix with three-dimensional structure of the present invention is maintained even after a long period passes since a remarkably great amount of enzymes compared with a known composite can be supported and immobilized to a matrix, and the immobilized enzyme is not easily released by an external impact. In addition, it is possible to stably immobilize a great amount of enzymes even if a functional group covalently bonding to enzymes is hardly present on the surface of fiber. Therefore, it is possible to remarkably improve performance by using the composite of enzyme and fiber matrix with three-dimensional structure of the present invention in a biosensor, a bio-fuel cell and the like, compared with the case using a known matrix composite.

7 Claims, 9 Drawing Sheets

COMPOSITE OF ENZYME AND FIBER MATRIX WITH THREE-DIMENSIONAL STRUCTURE, METHOD FOR PRODUCING THE SAME AND USE THEREOF

CROSS-REFERENCE TO RELATED APPLICATION

This application is a national stage application filed under 35 U.S.C. 371 of International Application No. PCT/KR2011/002785, filed Apr. 19, 2011, which claims priority from Korean Patent Application No. 10-2010-0047337, filed May 20, 2010, and Korean Patent Application No. 10-2011-0035980, filed Apr. 19, 2011, each of which is incorporated by reference herein in its entirety.

TECHNICAL FIELD

The present invention relates to a composite of enzyme and fiber matrix with three-dimensional structure, a method for producing the same, and use thereof. More specifically, the present invention relates to a composite of enzyme and fiber matrix with three-dimensional structure in which a significantly large amount of an enzyme is immobilized in/onto three-dimensional network structured fibers and the immobilized enzyme can be maintained stable for a long period of time, when compared to in conventional enzyme/three-dimensional network structured fiber matrix composites. The present invention also relates to a method for producing the composite, and use of the composite in biosensors, biofuel cells, enzyme columns, enzyme-linked immunosorbent assay (ELISA) kits, bioremediation devices, antifouling agents, and ibuprofen production.

BACKGROUND ART

Many methods, for example, carrier linking, crosslinking and absorption, have been proposed to effectively immobilize enzymes in/onto fibers having a three-dimensional network structure. With the advance of nanotechnology and increasing demand for nanobiotechnology electronics since the late 1990's, new enzyme immobilization methods have been needed and numerous results thereon have been presented. Based on the results, nanostructured materials have been developed. Under such circumstances, enzyme immobilization has received a great deal of attention for its applicability in biosensors, biofuel cells, enzyme columns, ELISA kits, bioremediation devices, antifouling agents, and ibuprofen production, etc.

An important key for the commercialization of immobilization of enzymes in/onto three-dimensional network structured fibers is how to maintain the stability of the enzymes while achieving high electrical performance. To this end, various nanostructured materials have been considered, for example, nanoporous materials, electrospun nanofibers and nanoparticles with large surface areas that prevent enzymes from leaching or falling out to maximize the loading of the enzymes when the enzymes are immobilized thereinto.

Enzyme immobilization methods using porous silica are divided into two methods, i.e. simple enzyme adsorption, and crosslinking after enzyme adsorption. The latter method provides better results in terms of stability than the former method, but there is no significant difference in activity between both methods because similar amounts of enzymes are adsorbed into silica. According to conventional methods for increasing the amount of enzymes immobilized into nanofibers, functional groups present on the surface of the nanofibers are covalently bonded to the enzymes, and crosslinkers are used to coat the enzymes on the nanofibers. However, the enzymes are immobilized in only limited amounts and are prone to denaturation. Another problem is that it is difficult to apply the methods to nanofibers having no surface functional groups capable of covalently bonding to the enzymes.

Consequently, the conventional methods for immobilizing enzymes in/onto three-dimensional network structured fibers have disadvantages of very low yield and poor long-term stability. Due to these disadvantages, the conventional methods are extremely difficult to commercialize.

DISCLOSURE

Technical Problem

The present invention has been made in an effort to solve the above problems, and it is a first object of the present invention to provide a method for stably immobilizing a significantly large amount of an enzyme in/onto a porous matrix including three-dimensional network fibers.

It is a second object of the present invention to provide a composite of enzyme and fiber matrix with three-dimensional structure in which a significantly large amount of an enzyme can be stably immobilized despite the substantial absence of functional groups capable of covalently bonding to the enzyme on the surface of three-dimensional network fibers.

Technical Solution

In order to achieve the first object of the present invention, there is provided a method for producing a composite of enzyme and fiber matrix with three-dimensional structure, the method including (1) adsorbing an enzyme onto a porous matrix including three-dimensional network fibers, (2) adding a precipitant to the enzyme-adsorbed matrix, and (3) adding a crosslinker to the resulting structures to form enzyme aggregates in which the precipitated enzyme molecules are crosslinked.

In a preferred embodiment of the present invention, the three-dimensional network fibers may be microfibers or nanofibers.

In a further preferred embodiment of the present invention, the three-dimensional network fibers may be selected from the group consisting of polyvinyl alcohol, polyacrylonitrile, nylon, polyester, polyurethane, polyvinyl chloride, polystyrene, cellulose, chitosan, polylactic acid, polylactic-co-glycolic acid, polyglycolic acid, polycaprolactone, collagen, polypyrrole, polyaniline, poly(styrene-co-maleic anhydride) fibers, and mixtures thereof.

In another preferred embodiment of the present invention, the enzyme aggregates may have a diameter larger than the size of the entrances of the pores.

In another preferred embodiment of the present invention, the enzyme molecules may form shells on the surface of the three-dimensional network fibers without the formation of substantial covalent bonds between the enzyme and the fibers.

In another preferred embodiment of the present invention, the surface of the three-dimensional network fibers may be unmodified.

In another preferred embodiment of the present invention, the precipitant may be selected from aqueous solutions of methanol, ethanol, 1-propanol, 2-propanol, butyl alcohol, acetone, polyethylene glycol (PEG), ammonium sulfate, sodium chloride, sodium sulfate, sodium phosphate, potassium chloride, potassium sulfate and potassium phosphate, and mixtures thereof.

In another preferred embodiment of the present invention, the crosslinker may include one or more compounds selected from the group consisting of diisocyanates, dianhydrides, diepoxides, dialdehydes, diimides, 1-ethyl-3-dimethylaminopropyl carbodiimide, glutaraldehyde, bis(imido esters), bis(succinimidyl ester), and diacid chlorides.

In another preferred embodiment of the present invention, the method may further include removing the precipitant and the crosslinker after step (3).

In order to achieve the second object of the present invention, there is provided a composite of enzyme and fiber matrix with three-dimensional structure, including: a porous matrix including three-dimensional network fibers; enzyme aggregates loaded in the pores of the matrix and having a diameter larger than the size of the entrances of the pores; and shells including an enzyme surrounding the surface of the three-dimensional network fibers.

In a preferred embodiment of the present invention, the three-dimensional network fibers may be microfibers or nanofibers.

In a further preferred embodiment of the present invention, the three-dimensional network fibers may be selected from the group consisting of polyvinyl alcohol, polyacrylonitrile, nylon, polyester, polyurethane, polyvinyl chloride, polystyrene, cellulose, chitosan, polylactic acid, polylactic-co-glycolic acid, polyglycolic acid, polycaprolactone, collagen, polypyrrole, polyaniline, poly(styrene-co-maleic anhydride) fibers, and mixtures thereof.

In another preferred embodiment of the present invention, the shells may be formed by crosslinking between the enzyme molecules.

In another preferred embodiment of the present invention, no substantial covalent bonds may be formed between the surface of the fibers and the shells.

According to another preferred embodiment of the present invention, there is provided a device selected from the group consisting of biosensors, biofuel cells, enzyme columns, ELISA kits, bioremediation devices, antifouling agents, and ibuprofen production, wherein the device includes the composite of enzyme and fiber matrix with three-dimensional structure.

The expression 'no substantial covalent bonding between the fibers and the enzyme' means that no functional groups are formed on the surface of the fibers, for example, by modification of the fiber surface, other than covalent bonds formed between functional groups naturally formed on the surface of the fibers and capable of covalently bonding to the enzyme (for example, amino groups remaining unreacted on the surface of the fibers during polymerization and spinning of the fibers) and the enzyme, and that no covalent bonds are formed between the fibers and the enzyme except for covalent bonds with functional groups naturally formed on the fiber surface.

Advantageous Effects

In comparison with conventional composites, the composite of enzyme and fiber matrix with three-dimensional structure of the present invention includes a significantly large amount of an enzyme loaded in and immobilized in/onto the fiber matrix. In addition, the immobilized enzyme is prevented from leaching from the fiber matrix when an external impact is applied to the composite. Therefore, the stability of the composite according to the present invention can be maintained even after the passage of a long period of time.

Even in the case of fibers having few or no functional groups participating in the formation of covalent bonds with the enzyme, a large amount of the enzyme can be stably immobilized on the surface of the fibers.

Therefore, the composite of enzyme and fiber matrix with three-dimensional structure of the present invention can be used to greatly improve the performance of biofuel cells, biosensors, electrical transistors and enzyme columns, and is useful in various applications, such as bioconversion, bioremediation, protein hydrolysis, drug synthesis, antifouling and quantitative analysis (ELISA), in comparison with conventional matrix composites.

BEST MODE

The present invention will now be described in more detail.

As described above, the conventional methods for effectively immobilizing enzymes on three-dimensional network structured fibers have disadvantages of very low yield and poor long-term stability. Due to these disadvantages, the conventional methods are extremely difficult to commercialize.

Further, enzymes are not substantially immobilized in/onto polyaniline nanofibers having few or no surface functional groups participating in the formation of covalent bonds with the enzymes.

In an effort to find a solution to the above problems, the present invention provides a method for producing a composite of enzyme and fiber matrix with three-dimensional structure, the method including (1) adsorbing an enzyme onto a porous matrix including three-dimensional network fibers, (2) adding a precipitant to the enzyme-adsorbed matrix, and (3) adding a crosslinker to the resulting structures to form enzyme aggregates in which the precipitated enzyme molecules are crosslinked. In comparison with conventional composites, a composite produced by the method of the present invention includes a significantly large amount of an enzyme loaded in and immobilized in/onto a matrix. In addition, the immobilized enzyme is prevented from leaching from the composite when an external impact is applied to the composite. Therefore, the stability of the composite can be maintained even after the passage of a long period of time. Even in the case of fibers having few or no functional groups participating in the formation of covalent bonds with the enzyme, a large amount of the enzyme can be stably immobilized on the surface of the fibers.

First, in step (1), an enzyme is adsorbed in/onto a porous matrix including three-dimensional network fibers. Any fibers that can form a three-dimensional network upon spinning to form pores therebetween may be used without limitation in the present invention. The fibers may be selected from the group consisting of polyvinyl alcohol, polyacrylonitrile, nylon, polyester, polyurethane, polyvinyl chloride, polystyrene, cellulose, chitosan, polylactic acid, polylactic-co-glycolic acid, polyglycolic acid, polycaprolactone, collagen, polypyrrole, polyaniline, polystyrene-co-maleic anhydride) fibers, and mixtures thereof. Polyaniline fibers are more preferred in terms of price and efficiency.

General polymerization and/or spinning processes, such as electrospinning and melt spinning, may be utilized for the production of the fibers so long as a three-dimensional network structure between the fibers is formed by the processes. The fibers may be nanofibers or microfibers depending on their diameter. Nanofibers are preferred taking into consideration the size of enzyme aggregates, which will be described later, and the size of pores formed between the fibers. The use of carbon nanotubes is outside the range of the present invention because carbon nanotubes cannot form a three-dimensional network when they are woven into fibers.

In an embodiment of the present invention, the porous matrix may include some or all of the three-dimensional network fibers. The term "porous" means the presence of pores (i.e. spaces) between the fibers forming a three-dimensional network.

The fibers may have a fiber matrix structure due to their ability to form a three-dimensional network. The matrix structure may be an amorphous structure in which the fibers are entangled intricately.

There is no restriction as to the kind of the enzyme. For example, any enzyme that can be adsorbed onto the surface of the fiber matrix according to the intended purpose of use may be used in the present invention. Examples of preferred enzymes suitable for use in the present invention, but are not limited to, chymotrypsin, trypsin, subtilisin, papain, lipase, horseradish peroxidase, soybean peroxidase, chloroperoxidase, manganese peroxidase, tyrosinase, laccase, cellulase, xylanase, lactase, sucrase, organophosphohydrolase, cholinesterase, glucose oxidase, alcohol dehydrogenase, glucose dehydrogenase, hydrogenase, and glucose isomerase. These enzymes may be used alone or as a mixture thereof.

The fiber matrix can be applied to fibers that substantially include no surface functional groups (for example, amino groups) capable of covalently bonding to the enzyme. Therefore, the enzyme is not covalently bonded to the surface of the fibers but is adsorbed onto the surface of the fibers or between pores (i.e. spaces) formed between the fibers. Therefore, when an external impact is applied to the composite, for example, the composite is washed with water in a state in which the enzyme is simply adsorbed onto the surface of the matrix, most of the adsorbed enzyme molecules fall out of the matrix, resulting in a marked reduction in the immobilization rate of the enzyme.

Next, in step (2), a precipitant is added to the enzyme-adsorbed matrix to prevent the enzyme from leaching out through pores of the matrix.

The adsorbed enzyme is too small to be substantially observed with the naked eye. The addition of the precipitant causes the adsorbed enzyme molecules to aggregate. As the aggregates of the enzyme molecules grow, the enzyme molecules are precipitated on the surface of the fibers or in the pores (i.e, spaces) formed between the fibers. Any precipitant that can precipitate the enzyme without substantially affecting the activity of the enzyme may be used without limitation in the present invention. The precipitant is preferably selected from aqueous solutions of methanol, ethanol, 1-propanol, 2-propanol, butyl alcohol, acetone, PEG, ammonium sulfate, sodium chloride, sodium sulfate, sodium phosphate, potassium chloride, potassium sulfate and potassium phosphate, and mixtures thereof.

Next, in step (3), a crosslinker is added to form enzyme aggregates in which the enzyme molecules are crosslinked. Since the precipitated enzyme is relatively small compared to pores (i.e. spaces) formed between the fibers, it may leach out through the pores when an external impact (e.g., washing) is applied to the composite. In order to prevent the enzyme leaching, the crosslinker is added to crosslink the precipitated enzyme molecules. The crosslinked enzyme molecules form aggregates to fill most of the pores. As a result, the size of the enzyme aggregates becomes larger than that of the entrances of the pores. With these dimensions, the enzyme is prevented from leaching out through the pores when an external impact is applied to the composite. In consequence, the enzyme aggregates are located within the pores despite the passage of time. Even though there are no direct bonds (for example, covalent bonds) between the fibers and the enzyme, the enzyme aggregates can be retained within the fiber matrix for a long period of time. In addition, the composite of enzyme and fiber matrix with three-dimensional structure includes a significant amount of the immobilized enzyme when compared to conventional composites. Therefore, the use of the composite of enzyme and fiber matrix with three-dimensional structure enables the fabrication of various devices, such as biosensors and biofuel cells, with markedly improved performance when compared to the use of conventional composites.

The addition of the crosslinker after treatment with the precipitant brings about greatly enhanced effects compared to the addition of the crosslinker only. If the crosslinker is added after enzyme adsorption without enzyme precipitation, significant parts of the pores formed between the fibers are not filled. Even though the pores are filled, the concentration of the enzyme molecules becomes equal to the ambient concentration. Therefore, the enzyme molecules present at the same concentration as the ambient concentration are not crosslinked sufficiently to form aggregates larger than the entrances of the pores in the nanofibers, which increases the probability that the crosslinked enzyme molecules may leach out during washing. In contrast, according to the method of the present invention, the enzyme molecules are forcibly packed into the pores of the nanofibers and are crosslinked to form larger aggregates. The bottle-neck or ship-in-a-bottle phenomenon is thus expected to cause less loss of EAPC than loss of EAC during washing.

The enzymes are not substantially immobilized on the surface of polyaniline nanofibers having few or no surface functional groups capable of covalently bonding to the enzymes. In the present invention, however, the enzyme molecules precipitated on the surface of the fibers are crosslinked to form shells surrounding the surface of the fibers. Therefore, even when covalent bonds are not substantially formed between the fibers and the enzyme, a large amount of the enzyme can form shells and can be immobilized on the surface of the fibers, like corn dogs.

Any crosslinker that does not inhibit the activity of the enzyme and can crosslink the enzyme molecules may be used without limitation in the present invention. The crosslinker is preferably selected from the group consisting of diisocyanates, dianhydrides, diepoxides, dialdehydes, diimides, 1-ethyl-3-dimethylaminopropyl carbodiimide, glutaraldehyde, bis(imido esters), bis(succinimidyl ester), diacid chlorides, and mixtures thereof. Glutaraldehyde is more preferred. However, it will be obvious to those skilled in the art that any crosslinker known in the art may be used without limitation.

After step (3), the composite of enzyme and fiber matrix with three-dimensional structure may be washed with water to remove the added crosslinker and precipitant. In matrix composites produced by general methods, most enzyme molecules immobilized between pores leach out through the pores by washing. In contrast, in the composite of enzyme and fiber matrix with three-dimensional structure produced by the method of the present invention, the enzyme can be prevented from leaching out through the pores and can be immobilized into the pores despite washing because the size of the enzyme aggregates is larger than that of the entrances of the pores.

According to a preferred embodiment, the present invention provides a composite of enzyme and fiber matrix with three-dimensional structure, including: a porous matrix including three-dimensional network fibers; enzyme aggregates loaded in the pores of the matrix and having a diameter larger than the size of the entrances of the pores; and shells including an enzyme surrounding the surface of the three-dimensional network fibers.

Figure 13:
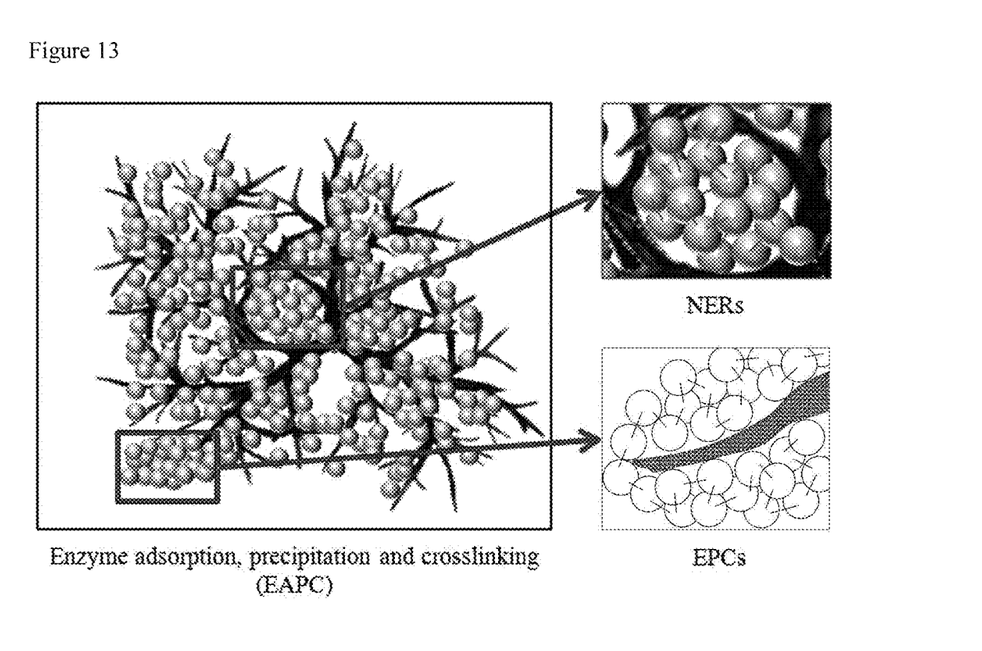
FIG. 13 shows a schematic diagram, a partial perspective diagram and a partial cross-sectional diagram of the composite of enzyme and fiber matrix with three-dimensional structure according to a preferred embodiment of the present invention.

FIG. 13 shows a schematic diagram, a partial perspective diagram and a partial cross-sectional diagram of an enzyme/three-dimensional network structured polyaniline nanofiber matrix composite according to a preferred embodiment of the present invention. As shown in FIG. 13, crosslinked enzyme aggregates are loaded in pores of the three-dimensional network structured fiber matrix because their diameter is larger than the size of the entrances of the pores. Shells including the enzyme aggregates surround the surface of the three-dimensional network fibers. The bottom right of FIG. 13 cross-sectionally shows a portion of the composite in which the shell including enzyme aggregates surrounds the surface of the three-dimensional network fiber, like a corn dog. No covalent bonds are formed between the fiber and the shell-forming enzyme aggregates.

In the composite of enzyme and fiber matrix with three-dimensional structure of the present invention, the enzyme aggregates have a size sufficient to prevent the enzyme from leaching out through the pores formed between the fibers. With these dimensions, the composite of the present invention includes a significantly large amount of the enzyme immobilized in/onto the matrix when compared to conventional enzyme composites. In other words, the size of the enzyme aggregates formed in the pores is larger than that of the entrances of the pores through which the enzyme aggregates may leach out. In consequence, the enzyme aggregates can be located within the pores even when an external stimulus (for example, washing) is applied to the composite. This allows the enzyme aggregates to be retained within the matrix for a long period of time without the formation of direct bonds between the enzyme and the matrix.

Enzymes are not substantially immobilized on the surface of polyaniline nanofibers having few or no surface functional groups capable of covalently bonding to the enzyme. In the present invention, however, the enzyme molecules precipitated on the surface of the fibers are crosslinked to form shells surrounding the surface of the fibers. Therefore, even when covalent bonds are not substantially formed between the fibers and the enzyme, a large amount of the enzyme can form shells and can be immobilized on the surface of the fibers, like hot dogs.

Finally, the activity of the enzyme can be expressed by the amount of the immobilized enzyme relative to the amount of the fibers used in the composite of enzyme and fiber matrix with three-dimensional structure. 5,000 to 6,000 units of enzyme are immobilized per g of fibers used in a conventional enzyme/three-dimensional network fiber matrix composite, whereas 50,000 to 60,000 units of enzyme are immobilized per g of the fibers used in the enzyme/three-dimensional network fiber matrix composite of the present invention. That is, a remarkably increased amount of the enzyme is immobilized in the composite of enzyme and fiber matrix with three-dimensional structure of the present invention.

In comparison with conventional composites, the composite of enzyme and fiber matrix with three-dimensional structure of the present invention includes a significantly large amount of the enzyme loaded in and immobilized in/onto the matrix.

In addition, the immobilized enzyme is prevented from leaching from the matrix when an external impact is applied to the composite. Therefore, the stability of the composite according to the present invention can be maintained even after the passage of a long period of time.

Even in the case of fibers having few or no functional groups participating in the formation of covalent bonds with the enzyme, a large amount of the enzyme can be stably immobilized on the surface of the fibers.

Therefore, the use of the composite of enzyme and fiber matrix with three-dimensional structure according to the present invention enables the fabrication of biosensors, biofuel cells, enzyme columns, ELISA kits, bioremediation devices, antifouling agents, and ibuprofen production with markedly improved performance when compared to the use of conventional matrix composites.

MODE FOR INVENTION

Preparative Example 1

Figure 1:
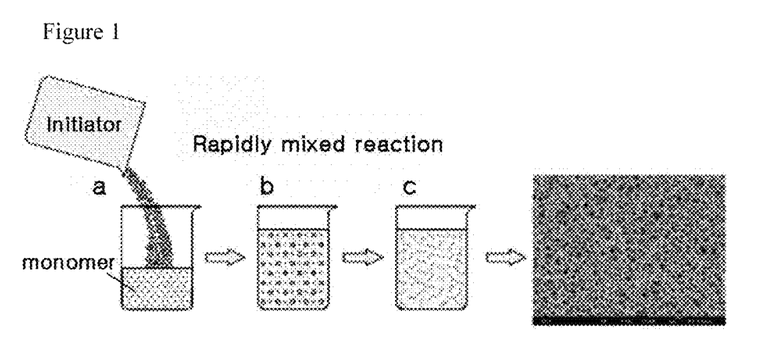
FIG. 1 is a schematic diagram showing a process for producing polyaniline nanofibers (PANFs)

Preparation of Three-Dimensional Network Structured Polyaniline Nanofiber Matrix A three-dimensional network structured polyaniline nanofiber matrix was prepared in accordance with the method shown in FIG. 1.

Specifically, electrically conductive polyaniline nanofibers (PANFs), into which an enzyme was immobilized, were prepared by oxidative polymerization using ammonium persulfate initiator as an oxidant. The oxidative polymerization was carried out using a rapidly mixing reaction by controlling the amount of the ammonium persulfate to prevent the overgrowth of polyaniline. Ammonium persulfate was dissolved in a 1 M HCl solution until the concentration reached 0.1 M. 1.5 ml of aniline was sufficiently stirred in 8.5 ml of 1 M HCl. 10 ml of the ammonium persulfate solution was completely mixed with 10 ml of the aniline/HCl solution. The resulting solution was stirred at 200 rpm and room temperature for 24 hrs. After the polymerization was finished, the reaction solution was centrifuged and the supernatant was discarded. The obtained PANFs were washed with a DI solution with stirring. This procedure was repeated several times. The polyaniline nanofibers were stored at 4° C. until use. The polyaniline nanofibers were synthesized by controlling the amount of the ammonium persulfate to prevent the over-growth of the nanofibers. The nanofibers were connected intricately to each other, like coral, to form a three-dimensional network structure. Depending on the aniline concentration, the nanofibers had pores therein as well as in the outer branches thereof. The pores of the nanofibers (i.e. the spaces created between the fibers) play a major role in subsequent enzyme immobilization. The polyaniline nanofibers were found to have a BET surface area of 58.4 $m^2/g$ and an average pore diameter of 12.26 nm. The total pore volume of the polyaniline nanofibers was 0.179 $cm^3/g$ (p/p0=0.990).

Comparative Example 1

Production of Enzyme/Three-Dimensional Network Structured Polyaniline Nanofiber Matrix Composite by Enzyme Adsorption (EA)

Figure 2:
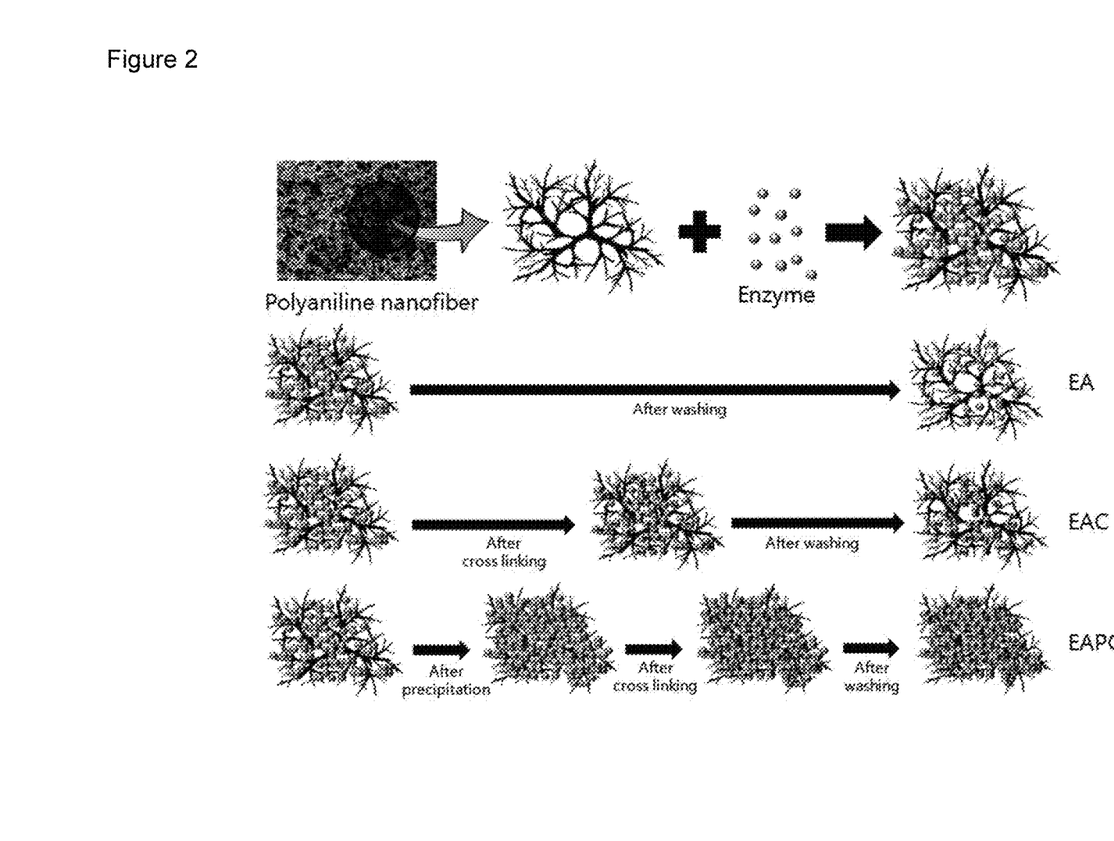
FIG. 2 is a schematic diagram showing processes for immobilizing enzymes on fiber matrixes.

An enzyme/three-dimensional network structured polyaniline nanofiber matrix composite was produced in accordance with the enzyme adsorption (EA) shown in FIG. 2. Specifically, 5 mg of the polyaniline nanofiber matrix prepared in Preparative Example 1 was added to 1 ml of a 10 mg/ml solution of glucose oxidase (GOx) in 100 mM PB buffer (pH 7.0) and stirred at 150 rpm for 2 hr. Thereafter, the solution including the GOx-adsorbed matrix composite was stirred using 100 mM Tris buffer (pH 7.4) at 200 rpm for 30 min and washed with 100 mM PB. After completion of all treatments, the enzyme-immobilized materials were stored at 4° C.

Comparative Example 2

Production of Enzyme/Three-Dimensional Network Structured Polyaniline Nanofiber Matrix Composite by Enzyme Adsorption and Crosslinking (EAC)

An enzyme/three-dimensional network structured polyaniline nanofiber matrix composite was produced in accordance with the enzyme adsorption and crosslinking (EAC) shown in FIG. 2. Specifically, the polyaniline nanofiber matrix prepared in Preparative Example 1 was washed with water and mixed with 1 ml of a 10 mg/ml GOx solution. The resulting mixture was stirred at 150 rpm for 2 hr to sufficiently adsorb the enzyme in/onto the nanofiber matrix. Thereafter, 20.4 μl of a 25% glutaraldehyde as a crosslinker was added to obtain a glutaraldehyde concentration of 0.5% (v/v). Then, the mixture was allowed to sufficiently react in a refrigerator at 4° C. for 17 hr. The solution including the matrix composite was stirred using 100 mM Tris buffer (pH 7.4) at 200 rpm for 30 min and washed with 100 mM PB. After completion of all treatments, the enzyme-immobilized materials were stored at 4° C.

Example 1

Production of Enzyme/Three-Dimensional Network Structured Polyaniline Nanofiber Matrix Composite by Enzyme Adsorption, Precipitation, and Crosslinking (EAPC)

An enzyme/three-dimensional network structured polyaniline nanofiber matrix composite was produced in accordance with EAPC shown in FIG. 2. Specifically, the polyaniline nanofiber matrix prepared in Preparative Example 1 was washed with water and mixed with a 10 mg/ml GOx solution. The resulting mixture was stirred at 150 rpm for 2 hr to sufficiently adsorb the enzyme in/onto the nanofiber matrix. Then, 1.4 ml of a 60% (w/v) ammonium sulfate solution as a precipitant was added to obtain a concentration of ammonium sulfate solution in the mixture of 35% (v/v). The resulting mixture was stirred at 150 rpm and room temperature for 30 min to facilitate the precipitation of the enzyme. Thereafter, a 25% (v/v) glutaraldehyde as a crosslinker was added in such an amount that the glutaraldehyde concentration was 0.5%. Then, the mixture was allowed to sufficiently react in a refrigerator at 4° C. for 17 hr. The solution including the matrix composite was stirred using 100 mM Tris buffer (pH 7.4) at 200 rpm for 30 min and washed with 100 mM PB. After completion of all treatments, the enzyme-immobilized materials were stored at 4° C.

Example 2

Identification of Degrees of Enzyme Immobilization in the Enzyme/Three-Dimensional Network Structured Polyaniline Nanofiber Matrix Composites The degrees of enzyme immobilization in the enzyme/three-dimensional network structured polyaniline nanofiber matrix composites produced in Example 1 and Comparative Examples 1 and 2 were identified by SEM.

Figure 3:
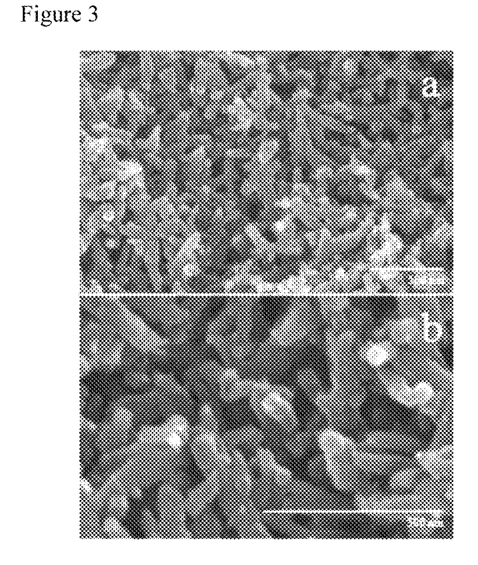
FIG. 3 shows SEM images of polyaniline nanofibers prepared in Preparative Example 1.
Figure 4:
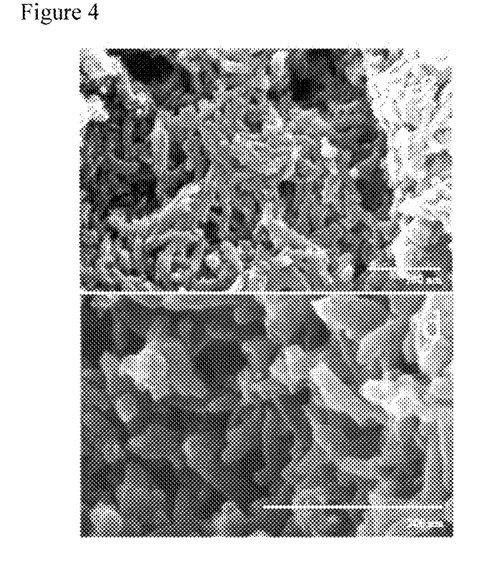
FIG. 4 shows SEM images of the composite of enzyme and fiber matrix with three-dimensional structure produced by enzyme adsorption (EA) in Comparative Example 1.
Figure 5:
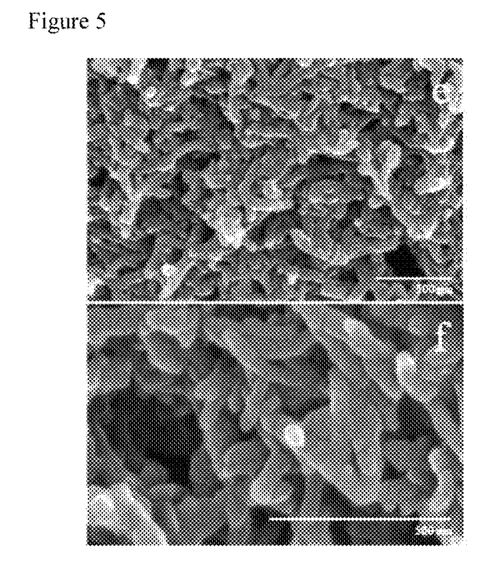
FIG. 5 shows SEM images of the composite of enzyme and fiber matrix with three-dimensional structure produced by enzyme adsorption and crosslinking (EAC) in Comparative Example 2.
Figure 6:
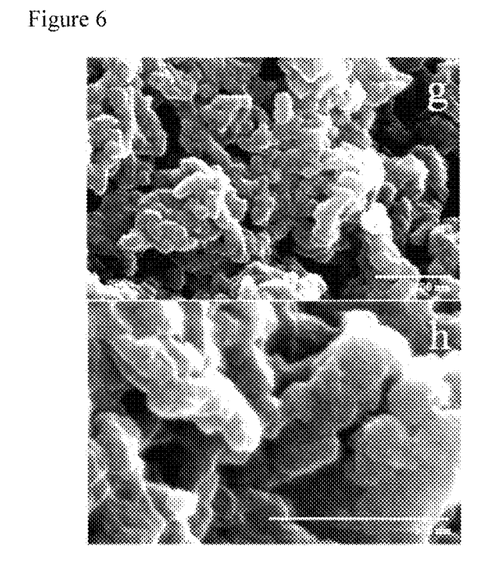
FIG. 6 shows SEM images of the composite of enzyme and fiber matrix with three-dimensional structure produced by enzyme adsorption, precipitation and crosslinking (EAPC) in Example 1.

Specifically, the SEM images of the polyaniline nanofibers (PANFs) prepared in Preparative Example 1 are shown in FIG. 3, the SEM images of the enzyme/three-dimensional network structured polyaniline nanofiber matrix composite produced by enzyme adsorption (EA) in Comparative Example 1 are shown in FIG. 4, the SEM images of the enzyme/three-dimensional network structured polyaniline nanofiber matrix composite produced by enzyme adsorption and crosslinking (EAC) in Comparative Example 2 are shown in FIG. 5, and the SEM images of the enzyme/three-dimensional network structured polyaniline nanofiber matrix composite produced by enzyme adsorption, precipitation and crosslinking (EAPC) in Example 1 are shown in FIG. 6.

As shown in FIGS. 3 to 6, there were no significant differences in the SEM images of the polyaniline nanofibers, EA, and EAC. However, the images of EAPC showed a considerable increase in the diameter of the polyaniline nanofibers compared to the other composites (FIG. 6). These results can be interpreted as follows. In EA and EAC, the GOx was immobilized into the pores of the polyaniline nanofibers without coating the polyaniline nanofibers. In EAPC, most of the enzyme molecules were present on the surface of the polyaniline nanofibers by precipitation and were coated by crosslinking to surround the surface of the polyaniline nanofibers. This result reveals that EAPC plays an important role in the degree of enzyme immobilization.

Example 3

Enzyme Activity and Stability Measurements in the Enzyme/Three-Dimensional Network Structured Polyaniline Nanofiber Matrix Composites The enzyme activities in the enzyme/three-dimensional network structured polyaniline nanofiber matrix composites produced in Comparative Examples 1 and 2 and Example 1 were measured using a UV spectrophotometer (UV-1800). Specifically, each of the enzyme/three-dimensional network structured polyaniline nanofiber matrix composites was diluted with 100 mM PB buffer to 0.1 mg/ml. 10 mg of o-dianisidine (ODS) was dissolved in 1.52 ml of DI and diluted with 100 mM PB buffer until the concentration of the ODS solution was 0.21 mM. D-glucose was added to the ODS solution to prepare a solution in which the D-glucose concentration was 1.724% (w/v). Peroxidase (POD) was dissolved in 100 mM PB buffer to prepare a solution having a concentration of 3.79 mg/ml. The three solutions were used to measure the activity of the enzyme. For the measurement of the enzyme activity, 980 μl of the ODS solution, 10 μl of the POD solution, and a solution of the polyaniline nanofiber matrix composite into which 10 μl of GOx was immobilized were mixed together, and the absorbance of the mixture was measured at 500 nm using a UV spectrophotometer.

Figure 7:
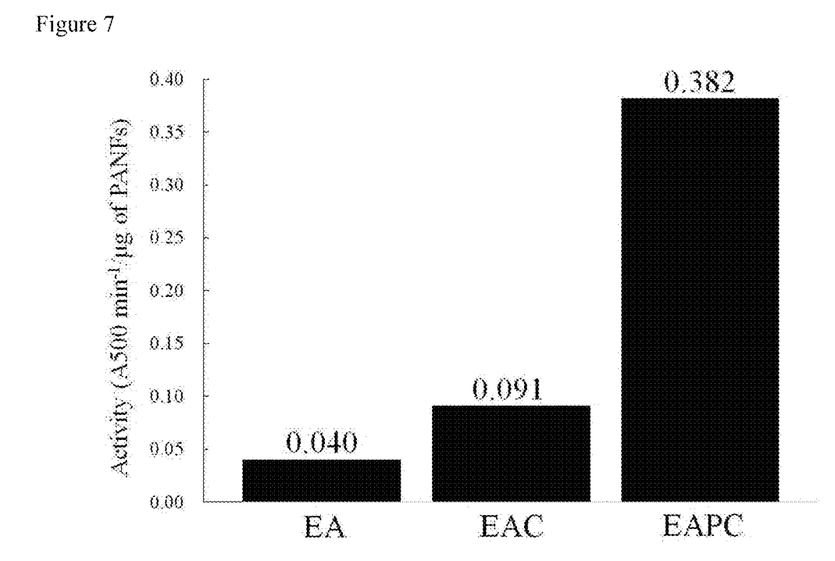
FIG. 7 graphically shows the activities of EA, EAC, and EAPC that were measured using a UV spectrophotometer.

FIG. 7 graphically shows the activities of EA, EAC, and EAPC using a UV spectrophotometer. The activities of EA, EAC, and EAPC were 0.040, 0.091, and 0.382 A500/min, respectively. The activity of EAPC was 9.6 and 4.2 times higher than the activities of EA and EAC, respectively. The increased activity of EAPC can be explained by the increased GOx loading, as can be seen from the SEM images of FIGS. 3 to 6. In EAPC, the enzyme precipitation made a large amount of the enzyme present on the surface of the polyaniline nanofibers and the addition of the crosslinker enabled coating of the enzyme, leading to immobilization of a larger amount of the enzyme.

Figure 8A:
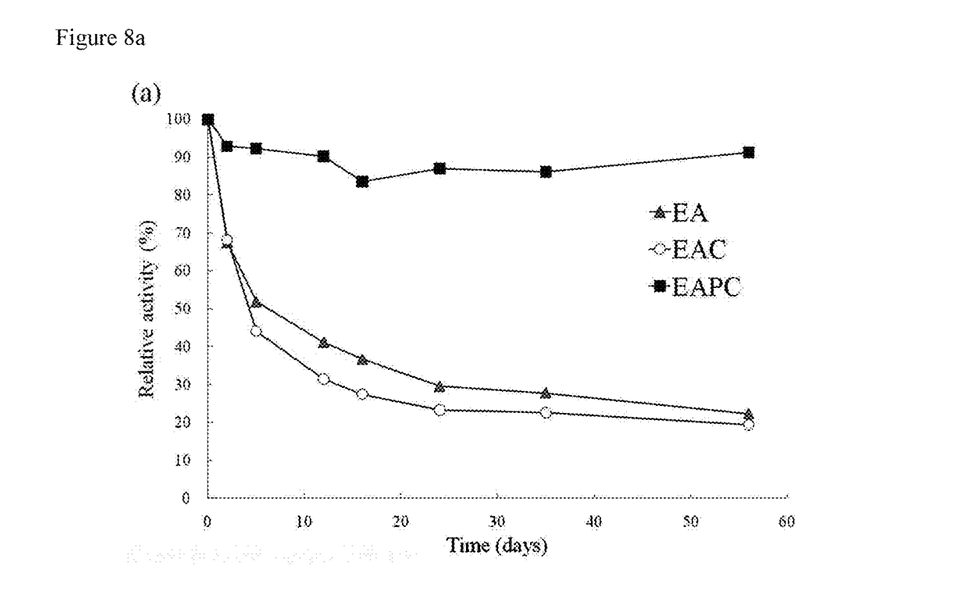
FIG. 8a graphically shows the stabilities of EA, EAC, and EAPC in 100 mM PB at room temperature under shaking at 200 rpm.
Figure 8B:
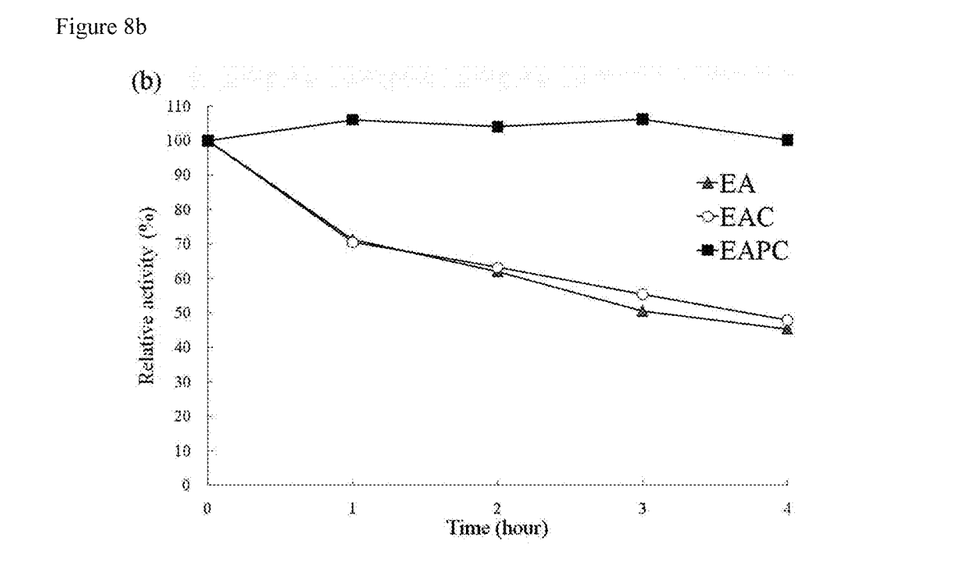
FIG. 8b graphically shows the stabilities of EA, EAC, and EAPC in 100 mM PB at 50° C. under shaking at 200 rpm to investigate the thermal stability thereof.

EAPC showed much better results in terms of activity than the other composites. FIG. 8a graphically shows the stabilities of composites in 100 mM PB at room temperature under shaking at 200 rpm. After 56 days, the activities of EA and EAC were 22% and 19% relative to the respective initial activities, whereas the activity of EAPC was maintained at a level of around 90% relative to the initial activity thereof. FIG. 8b graphically shows the activities of the composites in 100 mM PB at 50° C. under shaking at 200 rpm to investigate the thermal stability thereof. After 4 hr, the activities of EA and EAC dropped to a level of around 50%, while the activity of EAPC was maintained at a level of around 100%.

These results can be explained by the other strategies for the immobilization of GOx in/onto the polyaniline nanofibers. The simple adsorption (EA) and crosslinking after adsorption (EAC) failed to accomplish high loading of the enzyme in the polyaniline nanofibers and caused the immobilized enzyme molecules to fall out from the surface of the polyaniline nanofibers during the stability experiments. In contrast, the enzyme aggregates were fully packed in the pores of the polyaniline nanofibers in EAPC, revealing high enzyme loading. In addition, the fully packed enzyme aggregates did not readily leach out of the polyaniline nanofibers. As a result, it is expected that the use of the composite of enzyme and fiber matrix with three-dimensional structure of the present invention will contribute to a marked improvement in the performance of biofuel cells, etc.

Example 4

Production of Electrodes for Biofuel Cells Using the Enzyme/Three-Dimensional Network Structured Polyaniline Nanofiber Matrix Composites A 5% Nafion solution was added to a 3 mg/ml solution of each of the enzyme/three-dimensional network structured polyaniline nanofiber matrix composites produced in Comparative Example 1 and 2 and Example 1 until the concentration of Nafion reached 0.3%. The Nafion solution and the polyaniline nanofiber matrix composite solution were allowed to react with stiffing at 4° C. for 1 hr. Carbon papers (thickness=370 μm, area=0.332 cm$^2$) were dipped one at a time in the reaction solution and were allowed to stand at room temperature for 10 min for stable adsorption. The carbon papers were treated with a solution of sulfuric acid and nitric acid (3:1, v/v) before use. The adsorbed carbon papers were removed from the Nafion solution, dried at room temperature for 1 hr, washed several times with a 100 mM PB buffer, and stored at 4° C.

Example 5

Figure 9A:
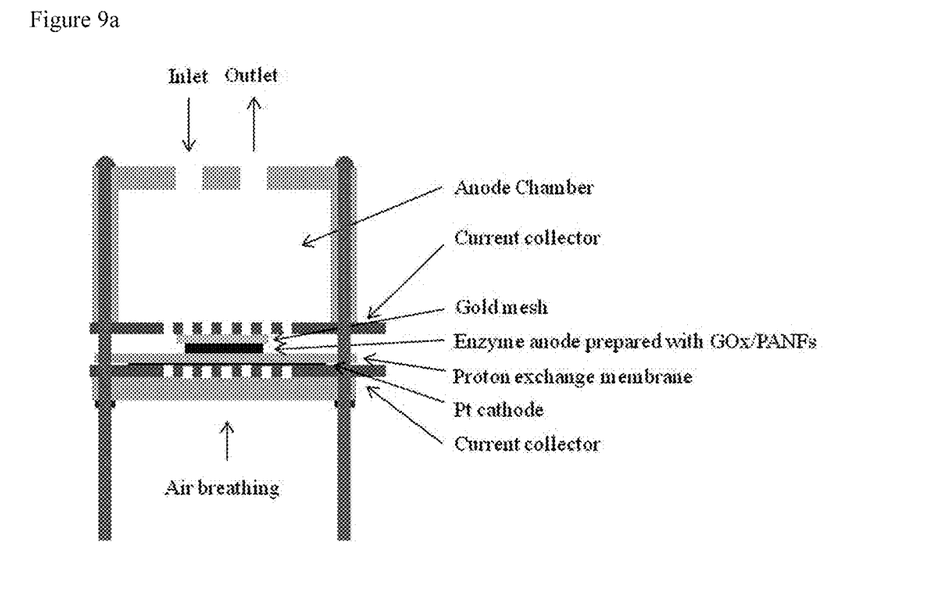
FIGS. 9a and 9b are a schematic diagram and a perspective view of a general fuel cell fabricated using a carbon paper produced in Example 4 as an anode.
Figure 9B:
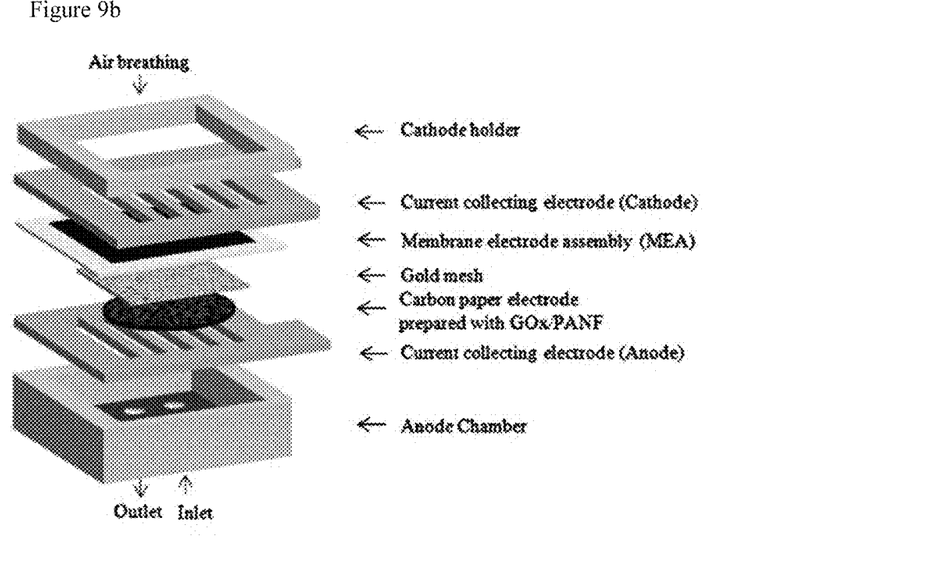
Figure 10:
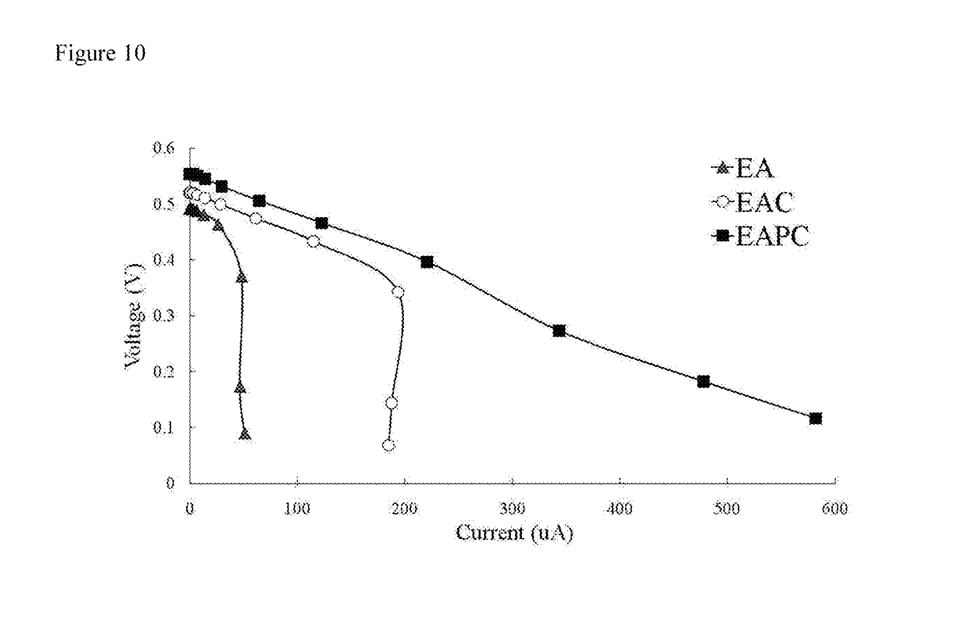
FIG. 10 shows polarization curves of a biofuel cell employing EA, a biofuel cell employing EAC, and a biofuel cell employing EAPC.

Fabrication of Biofuel Cells, and Polarization Curves and Electrochemical Impedance Measurements of the Biofuel Cells Biofuel cells were fabricated in accordance with general methods except that the enzyme-adsorbed carbon papers produced in Example 4 were used as anodes. Specifically constructions of the fuel cells are shown in FIGS. 9a and 9b. FIGS. 9a and 9b are a schematic diagram and a perspective view of a general fuel cell fabricated using the carbon paper produced in Example 4 as an anode. Specifically, the fuel cell includes an enzyme anode including the carbon paper, an anode chamber, a current collector, and a membrane electrode assembly (MEA). A cation exchange membrane, an air pump, and a Pt cathode were purchased from Fuel Cell Store (San Diego, Calif., USA). A 200 mM glucose solution as a fuel was supplied at a rate of 20 ml/min by means of a pump and a sufficient amount of air was supplied to the cathode.

10 mM 1,4-benzoquinone as a mediator for electron transfer was added to the glucose solution. The polarization curves, from which the maximum power densities can be calculated, were attained by using the mode of constant load discharge (CLD), in which an external resistance was applied to the biofuel cell from a resistance box. At each applied resistance, a time interval of 3 min was needed to obtain the stabilized current and voltage outputs. The obtained powers were divided by the surface area of the enzyme electrode (i.e., 0.33 cm$^2$) to calculate the power densities.

For analysis of the systems of the immobilized samples, Bio-Logic SP-150 was used to perform electrochemical impedance spectroscopy (EIS). The impedance spectra were taken in the frequency range from 20 Hz to 10 mHz with 10 steps per decade. The modulating voltage was 25 mV. A Nyquist plot was applied to display the impedance spectra. The diameter of a semicircle in the plot corresponds to the electron transfer resistance at the anode ($R_{et}$) and the intercept on the x-axis of the semicircle corresponds to the electrolyte resistance ($R_s$). To attain the values, a circuit model was used to consider the reaction kinetics of a biofuel cell in terms of Faradaic impedance. The EIS measurements were performed using the same reaction conditions as the polarization curve tests. For EIS measurements, hydrogen gas should be supplied instead of air to remove the effects of cathode resistance. In the present experiments, however, air was supplied instead of hydrogen because the cathode resistance was negligible relative to the total resistance.

Figure 11:
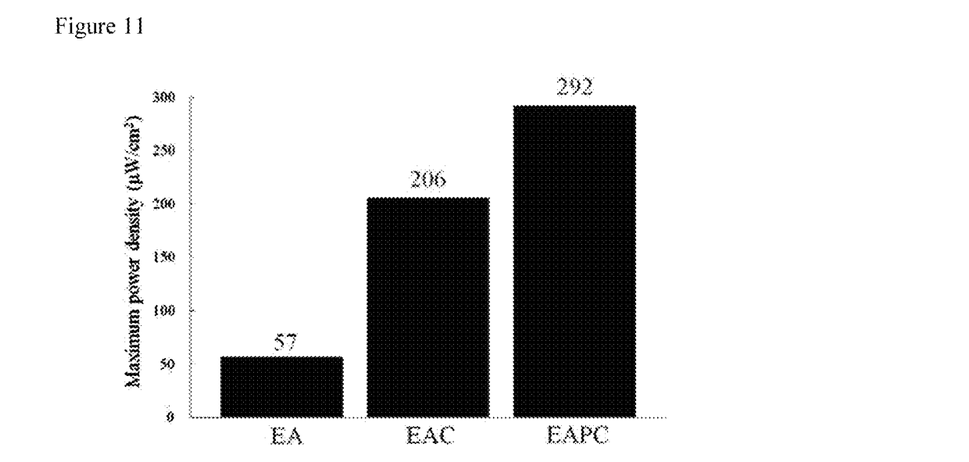
FIG. 11 graphically shows the initial maximum power densities of a biofuel cell employing EA, a biofuel cell employing EAC, and a biofuel cell employing EAPC.

The maximum power densities of the biofuel cells were measured by plotting the polarization curves using a 200 mM glucose solution as fuel. The initial maximum power densities of EA, EAC, and EAPC samples were measured to be 57, 206, and 292 µW/cm², respectively (FIG. 11). This suggests that the maximum power density of EAPC was 5 and 1.5 times higher than those of EA and EAC, respectively. When considering the respective activities and maximum power densities, there is an evident correlation between activity and maximum power density, but the improvement of maximum power density with the EAPC anode was less than the activity improvement. The enzyme activity is correlated with the enzyme amount while the maximum power density would be determined by both the electron generation and electron transfer rates. The enzyme activity correlates with the amount of the enzyme.

Figure 12:
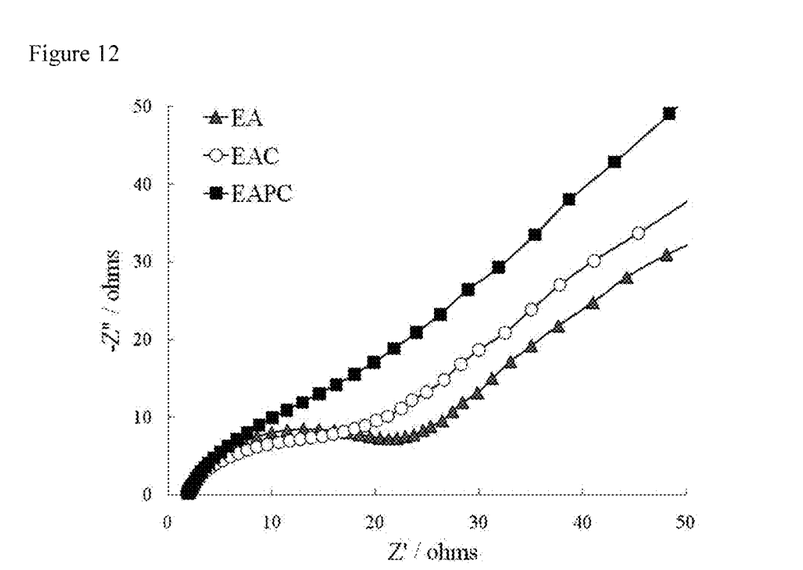
FIG. 12 is a graph showing the results of electrochemical impedance spectroscopy (EIS) for a biofuel cell employing EA, a biofuel cell employing EAC, and a biofuel cell employing EAPC.

To evaluate the resistances against electron transfer during the biofuel cell operation, the electrochemical impedance spectroscopy (EIS) measurements were performed and the results are shown in FIG. 12. A Nyquist plot attained through the EIS measurements could be used to calculate electrolyte resistance ($R_s$) and charge transfer resistance ($R_{ct}$). According to the Nyquist plot, the electrolyte resistance ($R_s$) was almost the same with all the samples. However, the charge transfer resistances ($R_{ct}$) of the EA, EAC, and EAPC anodes were 20.8, 18.3, and 43.4, respectively. The largest $R_{ct}$ value of the EAPC can be attributed to the high loading of enzyme molecules. The immobilization of a larger amount of the enzyme, a kind of protein, having a high resistance on the electrode leads to a larger charge transfer resistance. The $R_{ct}$ value of EAPC was about 2 times larger than that of EA and the maximum power density of EAPC was about 5 times higher than that of EA because of 9.6-fold higher activity of EAPC. In other words, the larger charge transfer resistance of EAPC retarded the electron transfer process, but the faster electron generation rate of EAPC, reflected on the enzyme activity data, resulted in the highest maximum power density.

The performance of the immobilized samples in the biofuel cells was tested using the polarization curves and EIS experiments. The stabilities of the enzyme electrodes were also tested in the same manner as in the enzyme-immobilized samples. The enzyme electrodes, each of which was produced by mixing Nafion with the immobilized sample and adsorbing the mixture to the carbon paper, were stored in 100 mM PB for stability experiments.

TABLE 1

|  |  | EA | EAC | EAPC |
|---|---|---|---|---|
| Initial operation | Maximum power density (µW/cm²) | 57 ± 5 | 206 ± 8 | 292 ± 24 |
|  | $R_s$ | 1.7 ± 0.2 | 1.6 ± 0.2 | 1.6 ± 0.2 |
|  | $R_{ct}$ | 20.8 ± 3.8 | 18.3 ± 3.6 | 43.4 ± 5.9 |
| 2 months at room temperature | Maximum power density (µW/cm²) | 70 ± 8 | 168 ± 35 | 311 ± 6 |
|  | $R_s$ | 1.7 ± 0.1 | 1.8 ± 0.1 | 1.7 ± 0.2 |
|  | $R_{ct}$ | 20.9 ± 2.7 | 23.3 ± 1.8 | 41.8 ± 1.0 |

Table 1 shows results of measurements for initial maximum power densities at room temperature and maximum power densities after 2 months. The initial maximum power densities of all enzyme electrodes were almost maintained even after storage for 2 months at room temperature. These results can lead to the conclusion that the adsorption of the enzyme-immobilized samples together with Nafion onto the carbon papers protected the enzyme from denaturation to some extent.

TABLE 2

|  |  | EA | EAC | EAPC |
|---|---|---|---|---|
| Initial operation | Maximum power density (µW/cm²) | 57 ± 5 | 206 ± 8 | 292 ± 24 |
|  | $R_s$ | 1.7 ± 0.2 | 1.6 ± 0.2 | 1.6 ± 0.2 |
|  | $R_{ct}$ | 20.8 ± 3.8 | 18.3 ± 3.6 | 43.4 ± 5.9 |
| 4 hours at 50° C. | Maximum power density (µW/cm²) | 70 | 233 | 319 |
|  | $R_s$ | 1.5 | 1.7 | 1.5 |
|  | $R_{ct}$ | 15.3 | 23.0 | 45.3 |

Table 2 shows results of measurements for initial maximum power densities at 50° C. and maximum power densities after 4 hr to investigate the thermal stability of the enzyme electrodes. As a result, the enzyme electrodes maintained their initial maximum power densities in all samples.

TABLE 3

|  |  | EA | EAC | EAPC |
|---|---|---|---|---|
| Initial operation | Maximum power density (µW/cm²) | 57 ± 5 | 206 ± 8 | 292 ± 24 |
|  | $R_s$ | 1.7 ± 0.2 | 1.6 ± 0.2 | 1.6 ± 0.2 |
|  | $R_{ct}$ | 20.8 ± 3.8 | 18.3 ± 3.6 | 43.4 ± 5.9 |
| 4 hours at 60° C. | Maximum power density (µW/cm²) | 32 ± 2 | 46 ± 3 | 315 ± 13 |
|  | $R_s$ | 1.7 ± 0.1 | 1.7 ± 0.1 | 1.7 ± 0.1 |
|  | $R_{ct}$ | 23.3 ± 3.3 | 24.9 ± 1.3 | 42.6 ± 0.2 |

Table 3 shows results of measurements for initial maximum power densities at 60° C. and maximum power densities after 4 hr to investigate the thermal stability of the enzyme electrodes. The initial maximum power density of EAPC was almost maintained, while the maximum power densities of EA and EAC dropped to 50% and 25%, respectively. In these experiments, it can be confirmed that the enzyme electrode produced using EAPC showed better stability.

INDUSTRIAL APPLICABILITY

The use of the composite of enzyme and fiber matrix with three-dimensional structure according to the present invention enables the fabrication of biosensors, biofuel cells, enzyme columns, ELISA kits, bioremediation devices, units for producing antifouling coatings (antifouling agents), and units for producing crystalline ibuprofen with markedly improved performance when compared to the use of conventional matrix composites.

The invention claimed is:
1. A composite of enzyme and fibers, comprising:
a plurality of polymeric fibers, wherein the polymeric fibers are intertwined to form a porous matrix; and
a plurality of enzyme aggregates comprising enzyme molecules crosslinked by a crosslinker,
wherein a first portion of the enzyme aggregates resides in pores of the porous matrix and a second portion of the enzyme aggregates forms shells over the polymeric fibers,
wherein no substantial covalent bonding exists between the enzyme aggregates and the polymeric fibers, and wherein the polymeric fibers are polyaniline fibers, polypyrrole fibers, or a mixture thereof, and no substantial functional groups exist on the surface of the polymeric fibers.

2. The composite according to claim 1, wherein the polymeric fibers are microfibers or nanofibers.

3. The composite according to claim 1, wherein the enzyme aggregates are formed in situ inside the porous matrix by crosslinking enzyme molecules so that the enzyme aggregates are immobilized within the porous matrix.

4. The composite according to claim 1, wherein no covalent bonding exists between the enzyme aggregates and the polymeric fibers.

5. The composite according to claim 1, wherein an activity of the composite decreases about 9% after 56 days in 100 mM phosphate buffer at room temperature under shaking at 200 rpm.

6. The composite according to claim 1, wherein an activity of the composite remains about the same after 4 hrs in 100 mM phosphate buffer at 50° C. under shaking at 200 rpm.

7. An enzyme-fiber composite, comprising:
a porous matrix comprising polymeric fibers, wherein the polymeric fibers are polyaniline fibers, polypyrrole fibers, or a mixture thereof, and have no substantial functional groups on the surface; and
a plurality of enzyme aggregates comprising enzyme molecules crosslinked by a crosslinker,
wherein a first portion of the enzyme aggregates resides in pores of the porous matrix and a second portion of the enzyme aggregates covers the polymeric fibers, and
wherein the polymeric fibers form no substantial covalent bonds with the enzyme aggregates.

* * * * *